(12) United States Patent
Ahmed

(10) Patent No.: US 11,174,107 B2
(45) Date of Patent: Nov. 16, 2021

(54) FLASH LAMP SYSTEM FOR DISINFECTING CONVEYORS

(71) Applicant: Xenon Corporation, Wilmington, MA (US)

(72) Inventor: Saad Ahmed, Wilmington, MA (US)

(73) Assignee: Xenon Corporation, Willmington, MA (US)

(*) Notice: Subject to any disclaimer, the term of this patent is extended or adjusted under 35 U.S.C. 154(b) by 0 days.

(21) Appl. No.: 16/827,099

(22) Filed: Mar. 23, 2020

(65) Prior Publication Data

US 2020/0299069 A1  Sep. 24, 2020

Related U.S. Application Data

(60) Provisional application No. 62/822,292, filed on Mar. 22, 2019.

(51) Int. Cl.
*B65G 45/10* (2006.01)
*B65G 15/28* (2006.01)
*A61L 2/10* (2006.01)

(52) U.S. Cl.
CPC .............. *B65G 45/10* (2013.01); *A61L 2/10* (2013.01); *B65G 15/28* (2013.01); *B65G 2201/0202* (2013.01); *B65G 2203/0291* (2013.01); *B65G 2207/26* (2013.01)

(58) Field of Classification Search
None
See application file for complete search history.

(56) References Cited

U.S. PATENT DOCUMENTS

| | | | |
|---|---|---|---|
| 4,871,559 | A | 10/1989 | Dunn et al. |
| 5,034,235 | A | 7/1991 | Dunn et al. |
| 5,364,645 | A | 11/1994 | Lagunas-Solar et al. |
| 5,489,442 | A | 2/1996 | Dunn et al. |
| 5,900,211 | A | 5/1999 | Dunn et al. |

(Continued)

FOREIGN PATENT DOCUMENTS

| | | |
|---|---|---|
| EP | 1020363 A2 | 7/2000 |
| WO | WO-02/090114 A1 | 11/2002 |

(Continued)

OTHER PUBLICATIONS

Bialka et al., "Decontamination of *Escherichia coli* O157:H7 and *Salmonella enterica* on Blueberries Using Ozone and Pulsed UV-Light," Journal of Food Science, vol. 72, Issue 9, 11 pages, first published Oct. 26, 2007.

(Continued)

*Primary Examiner* — Kavel Singh
(74) *Attorney, Agent, or Firm* — Leber IP Law; Sarah M. Gates

(57) ABSTRACT

A flash lamp system provides flashes to a bottom side of a conveyor to disinfect the conveyor while the conveyor is transporting products on a top side of the conveyor. The flashes are provided to discontinuous segments of the conveyor such that a portion of the conveyor is treated with each revolution, but a controller causes the entire length of the conveyor to be disinfected over multiple revolutions. The controller can respond to changes in speed and detected levels of disinfection. The disinfection system can be used in many applications, such as the transporting of fresh or frozen food products.

18 Claims, 2 Drawing Sheets

(56) References Cited

U.S. PATENT DOCUMENTS

| | | | |
|---|---|---|---|
| 6,132,784 A * | 10/2000 | Brandt | A23B 7/015 422/186.3 |
| 6,228,332 B1 | 5/2001 | Dunn et al. | |
| 6,245,711 B1 | 6/2001 | Halbrook, Jr. | |
| 6,453,145 B1 | 9/2002 | Miura | |
| 6,492,645 B1 | 12/2002 | Allen et al. | |
| 6,730,923 B1 * | 5/2004 | May | A61L 2/10 250/435 |
| 7,234,586 B1 * | 6/2007 | Newman | A23G 9/30 198/495 |
| 7,638,780 B2 * | 12/2009 | Kilburn | F26B 3/28 118/620 |
| 7,845,823 B2 * | 12/2010 | Mueller | H05B 45/20 362/231 |
| 8,624,203 B2 * | 1/2014 | Tullo | A61L 2/10 250/492.1 |
| 2002/0162971 A1 | 11/2002 | Koenck et al. | |
| 2003/0145664 A1 | 8/2003 | Schwarz et al. | |
| 2003/0198716 A1 | 10/2003 | Hankinson et al. | |
| 2004/0028553 A1 | 2/2004 | Panico | |
| 2007/0196235 A1 * | 8/2007 | Shur | A23L 3/28 422/62 |
| 2008/0075629 A1 * | 3/2008 | Deal | A61B 90/70 422/24 |
| 2009/0304880 A1 | 12/2009 | Kidder et al. | |
| 2010/0007577 A1 | 1/2010 | Ninan et al. | |
| 2010/0098874 A1 | 4/2010 | Schroder | |
| 2010/0183779 A1 * | 7/2010 | Felix | A23B 7/015 426/231 |
| 2010/0223843 A1 | 9/2010 | Williams | |
| 2011/0091579 A1 | 4/2011 | Hausman | |
| 2012/0051046 A1 | 3/2012 | Jackson | |
| 2012/0079950 A1 | 4/2012 | Schroeder | |
| 2014/0042342 A1 | 2/2014 | Karim et al. | |
| 2014/0227132 A1 | 8/2014 | Neister | |
| 2015/0151014 A1 | 6/2015 | Vasilenko | |
| 2018/0110890 A1 | 4/2018 | Matsui | |
| 2018/0343898 A1 | 12/2018 | Alzeer et al. | |
| 2019/0320670 A1 | 10/2019 | Hathaway et al. | |
| 2020/0299069 A1 | 9/2020 | Ahmed | |

FOREIGN PATENT DOCUMENTS

| | | |
|---|---|---|
| WO | WO-03/061382 A1 | 7/2003 |
| WO | WO-2010/105365 A1 | 9/2010 |
| WO | WO-2014/026187 | 2/2014 |
| WO | WO-2019/204627 | 10/2019 |
| WO | WO-2020/198138 | 10/2020 |

OTHER PUBLICATIONS

International Search Report and Written Opinion dated Jul. 28, 2020, in the International Application No. PCT/US20/24208, 15 pages.

International Search Report and Written Opinion dated Jul. 5, 2019, in the International Application No. PCT/US19/28156, 14 pages.

* cited by examiner

FLASH LAMP SYSTEM FOR DISINFECTING CONVEYORS

CROSS-REFERENCE TO RELATED APPLICATIONS

This application claims priority to U.S. Provisional Patent Application 62/822,292, titled "Flash Lamp System for Disinfecting Conveyors," filed Mar. 22, 2019, the content of which is incorporated herein by reference in its entirety.

TECHNICAL FIELD

This disclosure relates to generally to flash lamp systems, and in particular to a flash lamp system for treating and disinfecting a conveyor.

BACKGROUND

Ultraviolet (UV) radiation can be used for many purposes, including sterilizing and disinfecting water, food, packaging, and other objects (such as mail or keyboards), or for curing or annealing materials, such as adhesives or coatings, or sintering conductive inks. UV radiation can be provided in a continuous manner (e.g., with a mercury lamp) with relatively lower power over a longer duration, or with one or more flashes or pulses of high-intensity, short duration UV energy from a xenon flash lamp. One advantage of flash lamp systems is that the high-power, short duration flashes do not heat up workpieces or substrates as much as continuous-operation mercury lamps can.

Flash lamps provide UV energy with a broad range of wavelengths/frequencies. For disinfection, there is a germicidal range of UV energy with wavelengths from about 100 nm to over 300 nm, with a peak effectiveness in a wavelength range of about 250-280 nm. With sufficient energy density ($mJ/cm^2$) at these wavelengths (also referred to as a "dose"), the UV energy disrupts the DNA of viruses, bacteria, and protozoa to a desired confidence level. See, e.g., U.S. Patent Application Publication No. 2004/0028553, assigned to Xenon Corporation, which is incorporated herein by reference.

SUMMARY OF THE INVENTION

Systems and methods are disclosed herein for treating and disinfecting a conveyor during operation in which items are transported in a substantially continuous manner in revolutions, the conveyor including an operating area where items are transported and a separate treatment area where the conveyor is treated to disinfect the conveyor. In some embodiments, the system includes a flash lamp system for providing flashes of energy from at least one light source to the treatment area of a conveyor and a flash lamp controller configured to control a timing of the flashes so that the flashes are provided to discontinuous segments of the conveyor during each revolution, such that over multiple revolutions, all segments of the conveyor obtain a desired level of energy sufficient for disinfection. In some embodiments, the flash lamp controller is responsive to information relating to a linear speed of the conveyor, for changing the timing of flashes in response to changes in the linear speed.

In some embodiments of the present disclosure, the flash lamp controller is responsive to information regarding a disinfection level of the conveyor, for altering one or more of energy and flash timing based on the disinfection level. In some embodiments, the systems or methods also include a second flash lamp system for providing flashes of energy to products in the operating area and/or the at least one light source is directed to a bottom return side of the conveyor. In other embodiments, the systems or methods include a conveyor speed sensor system, wherein the flash lamp controller receives speed information from the speed sensor system, wherein the speed sensor senses one or more of a conveyor belt speed, rotations of a conveyor roller, and a translation rate of the conveyor. In some embodiments, the systems or methods include a conveyor having a top side for transporting products, and a bottom side, wherein the flash lamp system is positioned to provide energy to the bottom side of the conveyor.

These and other capabilities of the disclosed subject matter will be more fully understood after a review of the following figures, detailed description, and claims. It is to be understood that the phraseology and terminology employed herein are for the purpose of description and should not be regarded as limiting.

BRIEF DESCRIPTION OF FIGURES

Various objectives, features, and advantages of the disclosed subject matter can be more fully appreciated with reference to the following detailed description of the disclosed subject matter when considered in connection with the following drawings, in which like reference numerals identify like elements.

DETAILED DESCRIPTION

Figure 1:
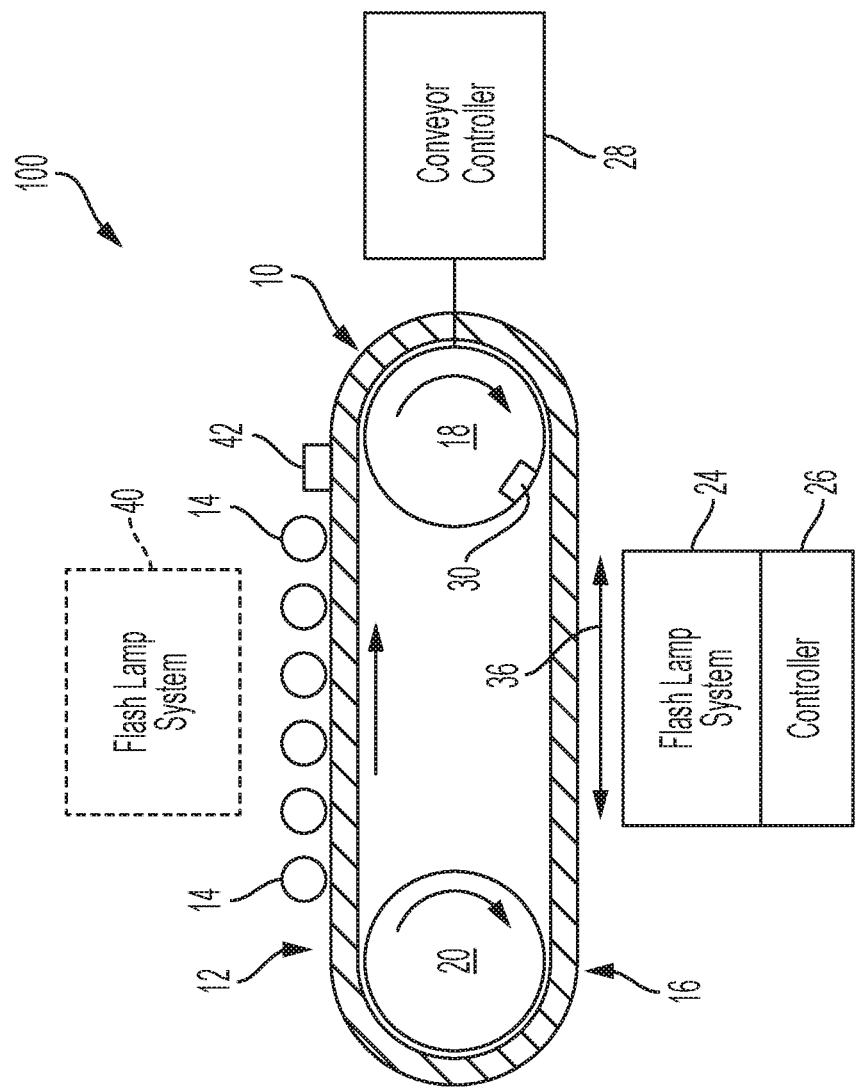
FIG. 1 shows a conveyor sterilization system, according to some embodiments of the present disclosure.

Referring to FIG. 1, the embodiments described herein relate to systems and methods for treating a conveyor for items and can be used while the conveyor is being used to transport the items in normal operation, such as transporting items for inspection, UV treatment, or packaging, as opposed to a separate sterilization process. The systems and methods for disinfecting the conveyor can be used with or without a flash lamp system used for treating the items themselves. The systems and methods can be used with different types of conveyors, such as a belt conveyor or a metallic mesh.

One way to disinfect a conveyor would be to stop the operation of the conveyor and implement a disinfection process. However, this approach would require that the conveyor be shut down and allow contamination between cleanings.

FIG. 1 shows a conveyor sterilization system 100, according to some embodiments of the present disclosure. A conveyor 10 is represented as being used with a front roller 18 and a rear roller 20 and having a top side 12 for moving items 14, and a bottom return side 16. To simplify, and for purposes of explanation, assume that the front roller 18 is a drive roller for causing the conveyor 10 to move in the longitudinal direction, and the rear roller 20 is a passive, non-driven roller. In some embodiments, the roles of front roller 18 and rear roller 20 may be reversed such that rear roller 20 serves as the drive roller and front roller 18 is a passive, non-driven roller. In other embodiments, both rollers 18 and 20 may be serve as drive rollers in conveyor sterilization system 100. A system could also have other numbers of rollers and other geometry. For example, three rollers arranged in a triangular manner, or four arranged in a rectangle.

Conveyor 10 may be used to transport any items and conveyor 10 may be used for any purpose. In one embodiment, where disinfection might be highly desired would be with food products that come into direct contact with the conveyor, e.g., frozen meatballs or fresh blueberries. In this case, it would be desirable to disinfect the conveyor 10 so that microbes on the conveyor do not contaminate the food products.

In some embodiments, a flash lamp system 24 for disinfecting the conveyor 10 is placed under conveyor 10 facing the bottom return side 16 to treat the conveyor 10 at a location separate from the location of items 14. In some embodiments, flash lamp system 24 could include one lamp or a bank of lamps (not shown) in a one-dimensional or two-dimensional array. See, e.g., U.S. Patent Application Publication No. 2014/0042342, assigned to Xenon Corporation, incorporated herein by reference.

The number of lamps and frequency at which the lamps are flashed, also referred to herein as a flash initiation time, may depend on the desired level of sterility for conveyor 10. It would be possible to have a sufficient number of lamps and/or sufficient frequency of flashes so that the conveyor is continuously disinfected. Increasing the number of lamps and flash initiation time allows the operator to achieve a desired sterility assurance level. In some embodiments, conveyor sterilization system 100 may result in a sterility assurance level of $10^{-4}$. The frequency at which flash lamp system 24 flashes may be based on the flash initiation time as set by an operator. The flash initiation time may be a predetermined, constant time interval or a variable time interval based on the translational speed of conveyor 10, described further below. In some embodiments, the increased number of lamps in flash lamp system 24 would result in higher costs of operation and would be more energy-intensive than necessary or desired. Similarly, an increased frequency of operation of flash lamp system 24 would also result in higher costs of operation and would be more energy-intensive.

The flash lamp system 24 further includes a flash lamp controller 26 that causes flash lamp system 24 to flash at desired times. The flash lamp controller 26 may receive information regarding the speed at which conveyor 10 is circulating. Such information may include, among others, the number of rotations per second of front roller 18 or rear roller 20, the translational rate of conveyor 10 measured in distance divided by a unit time, or the number of items 14 passing past a specific point of conveyor sterilization system 100. This information could come from a direct or indirect connection to a conveyor controller 28 that drives the conveyor, or from a sensor, represented at 30, that can be built into, or added to, the conveyor sterilization system 100, e.g., at either one of front roller 18 or rear roller 20.

Flash lamp system 24 can disinfect over a treatment area 36 of conveyor 10. Treatment area 36 of conveyor 10 may be defined by the entire width of conveyor 10 over a longitudinal, linear distance along conveyor 10. In other embodiments, treatment area 36 of conveyor 10 may be defined by a width of conveyor 10 less than the entire width over a longitudinal, linear distance along conveyor 10. Flash lamp controller 26 uses information about the linear distance of treatment area 36 and the conveyor 10 speed to determine an appropriate flash initiation time such that flash lamp system 24 flashes at appropriate times to disinfect conveyor 10 completely for a set number of revolutions of conveyor 10. In some embodiments, the flash initiation time may be set by flash lamp controller 26 based on the translational speed of conveyor 10. In other embodiments, flash lamp controller 26 may adjust the flash lamp initiation time to coincide with changes in the speed of conveyor 10.

For example, assume conveyor 10 has a total length of 10 meters, and the flashes from the flash lamp system 24 disinfect 1 meter of the linear distance across the entire width of the conveyor 10. The flash lamps in flash lamp system 24 could flash twice for every revolution of conveyor 10 to ensure that the entire surface area conveyor is treated every five revolutions, or at appropriate times for disinfection every three, or eight, or any desired number of revolutions of conveyor 10. If treatment to the conveyor 10 is provided with two flashes per revolution, and treated every five revolutions, the flash initiation times need to be set so that ten different linear meters are being treated over the course of five revolutions.

Figure 2:
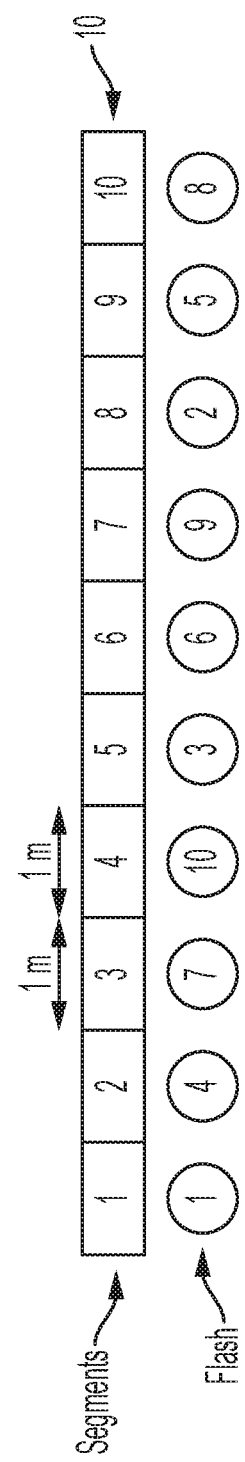
FIG. 2 shows a conveyer, according to some embodiments of the present disclosure.

The flash initiation times can be divided to avoid overlap so the frequency is constant for a constant conveyor speed. For example, FIG. 2 shows conveyor 10 as if it were virtually cut transversely and laid out in ten individual linear segments, numbered one through ten, of one meter each. In this example, the lamps flash every time the conveyor travels 70% of conveyor's 10 linear distance. In this case, meters #1 and #8 of conveyor 10 would be treated by flash lamp system 24 at flash instances #1 and #2 in the first revolution, meter #5 would be treated by flash lamp system 24 at flash instance #3 in the second revolution, and so forth with the remaining meter segments with corresponding flash instances until all ten meters of conveyor 10 were treated with flash instances over the course of seven full revolutions. In other words, the flashes are provided to separated sections of the conveyor. An operator may set other time intervals for flash initiation times as a function of the longitudinal, linear distance of conveyor 10 and the desired number of revolutions necessary to disinfect the entire linear distance of conveyor 10. For example, an operator could program flash instances for every 33% of the conveyor's 10 linear distance, in which case the conveyor is fully treated approximately every three revolutions.

Using the conveyor speed information as received by conveyor controller 28 or sensor 30, conveyor sterilization system 100 can compensate for different conveyor 10 speeds in different applications. For example, conveyor sterilization system 100 may be modified by an operator for different forms of treatment to the items or for different types of items, and/or can adjust in real time in response to changes in the line speed of the conveyor's rotation during operation. For example, conveyor sterilization system 100 may be used in conjunction with other disinfection treatment methods depending on the needs of an operator or to supplement pre-existing disinfecting systems.

Referring back to FIG. 1, in another embodiment, the conveyor sterilization system 100 can be used while a second flash lamp system 40 is used to treat items on the top side 12 of conveyor 10. In other embodiments, conveyor 10 may be used for other purposes than those described above with respect to FIG. 1, such as for optical inspection of items 14 or to transport items 14 to another location (e.g., to a packaging process, or as part of a counting process, etc.). Additional conveyors or systems for packaging or other purposes are not shown.

A sensor 42 could be provided in conveyor 10 and coupled directly or indirectly to controller 26 to allow the system to ensure that flash lamp system 24 and/or second flash lamp system 40 are effectively disinfecting the conveyor 10 as expected by an operator. Controller 26 may receive information from sensor 42 via wired or wireless means including. Sensor 42 may comprise a single sensor element at a single point in conveyor 10 or multiple sensors at different locations in conveyor 10.

Controller 26 can include any special-purpose or general-purpose hardware and software for controlling aspects of the system, such as a microprocessor, microcontroller, field programmable gate array ("FPGA"), volatile and non-volatile memory, among others, and can represent multiple interconnected controllers. While shown separately, one controller could be used for conveyor 10 and for flash lamp system 24 and second flash lamp system 40. In some embodiments, controller 26 may control communicate with conveyor 10, flash lamp system 24, and second flash lamp system 40 through wired and wireless connections such as an access control system, programmable logic controller, proportional integral derivative controller, or a computing device in a local area network (LAN). Wireless connections may include a wide-area network (WAN), wireless local area network (WLAN) connections, Bluetooth, or IR wireless connection and may be operated over cloud-based or distributed networks.

Embodiments of the present disclosure relate to systems for disinfecting a conveyor with a flash lamp system, including while the conveyor is in normal working operation; methods for disinfecting a conveyor with a flash lamp system, including while the conveyor is in normal working operation; systems and methods for disinfecting a conveyor that can disinfect a conveyor over multiple revolutions of a conveyor, and can adjust the frequency from time to time or on the fly; systems and methods for disinfecting a conveyor that can compensate for different rates of speed, including on the fly; systems and methods for disinfecting a conveyor that can include a sensor for detecting that a portion of the conveyor has been treated.

Various other modifications, including additions and removals, can be made to the exemplary embodiments discussed without departing from the scope of the present disclosure. For example, while the embodiments described above refer to particular features, components, or particular steps, the scope of this disclosure also includes embodiments having different combinations of features, components, or steps, and embodiments that do not include all of the above described features, components, or steps. Terms such as "above" and "below" are used as relative terms, and not in an absolute sense.

It is to be understood that the disclosed subject matter is not limited in its application to the details of construction and to the arrangements of the components set forth in the description or illustrated in the drawings. The disclosed subject matter is capable of other embodiments and of being practiced and carried out in various ways. For example, while the conveyor is shown as having two rollers such that the conveyor is parallel in its top and return tracks, the disclosed system could include three or more rollers in a triangular or other cross-sectional shape. Also, it is to be understood that the phraseology and terminology employed herein are for the purpose of description and should not be regarded as limiting. All documents referred to here, including without limitation patents and publications assigned to Xenon Corporation, are incorporated herein by reference in their entireties and for all purposes. The systems described in these prior publications could be used in whole or in part with the systems disclosed here.

The invention claimed is:

1. A system for treating and disinfecting a conveyor during operation in which items are transported in a substantially continuous manner in revolutions, the system comprising:
    a flash lamp system for providing a series of high-intensity, short-duration flashes of energy from at least one light source to a treatment area of the conveyor, the treatment area including an area of the conveyor where the conveyor is treated to disinfect the conveyor separate from an operating area of the conveyor where the items are transported; and
    a flash lamp controller configured to control a frequency of the flashes based on a combination of a translational speed of the conveyor, a linear distance of the treatment area, and a flash illumination area so that the flashes are provided to discontinuous segments of the conveyor during each revolution, such that over a set number of multiple revolutions, all segments of the conveyor obtain a desired level of energy sufficient for disinfection of a complete length of the conveyor.

2. The system of claim 1, wherein the flash lamp controller is configured to change the frequency of the flashes in response to changes in the translational speed of the conveyor such that the complete length of the conveyor is disinfected over the same set number of multiple revolutions.

3. The system of claim 1, wherein the flash lamp controller is responsive to information regarding a disinfection level of the conveyor, for altering at least one member of a group consisting of flash energy and the frequency of the flashes based on the disinfection level.

4. The system of claim 1, further comprising a second flash lamp system for providing flashes of energy to products in the operating area.

5. The system of claim 1, wherein the at least one light source is directed to a bottom return side of the conveyor.

6. The system of claim 2, further comprising a conveyor speed sensor system, wherein the flash lamp controller receives information relating to the translational speed of the conveyor from the speed sensor system, wherein the speed sensor senses at least one member of a group consisting of a conveyor belt speed, rotations of a conveyor roller, and a translation rate of the conveyor.

7. The system of claim 1, further comprising the conveyor having a top side for transporting the items, and a bottom side, wherein the flash lamp system is positioned to provide the flashes of energy to the bottom side of the conveyor.

8. The system of claim 1 further comprising the conveyor.

9. A method for treating and disinfecting a conveyor during normal operation in which items are transported in a substantially continuous manner in revolutions, the method comprising:
    providing, to a treatment area of the conveyor, a series of flashes of ultraviolet energy with a flash lamp system having at least one light source, the treatment area including an area of the conveyor where the conveyor is treated to disinfect the conveyor separate from an operating area of the conveyor where items are transported;
    monitoring a translational speed of the conveyor; and
    controlling a frequency of the flashes based on a combination of the translational speed of the conveyor, a linear distance of the treatment area, and a flash illumination area, such that flashes are provided to discontinuous segments of the conveyor during each revolution in a manner that over a set number of multiple revolutions, all segments of the conveyor obtain a desired level of energy sufficient for disinfection of a complete length of the conveyor.

10. The method of claim 9, wherein the controlling includes changing the frequency of flashes in response to changes in the translation speed of the conveyor such that the complete length of the conveyor is disinfected over the same set number of multiple revolutions.

11. The method of claim 9, wherein the controlling includes altering at least one member of a group consisting of flash energy and the frequency of the flashes based on information relating to a disinfection level of the conveyor.

12. The method of claim 9, wherein the providing includes providing flashes to a conveyor used to transport fresh food products.

13. The method of claim 9, wherein the providing includes providing flashes to a conveyor used to transport frozen food products.

14. The method of claim 9, wherein the treatment area is on a lower bottom side of the conveyor, the method further comprising providing flashes with a flash lamp system to the items transported on a top side of the conveyor while also providing disinfecting flashes to the bottom side.

15. A system comprising:
a conveyor having a top side for transporting products in a substantially continuous manner, and a bottom side;
a flash lamp system having at least one flash lamp for providing a series of high-intensity, short-duration flashes of ultraviolet (UV) energy to the bottom side of the conveyor to disinfect the conveyor; and
a flash lamp controller for controlling the flash lamp system to cause the flashes to be provided to disconnected segments of the conveyor during each revolution of the conveyor, while also controlling the flash lamp system based on a combination of a translational speed of the conveyor, a length of the conveyor, and a flash illumination area to provide a sufficient number of flashes and amount of UV energy for disinfection of all segments of the conveyor over a set number of revolutions of the conveyor.

16. The system of claim 15, wherein the conveyor receives one of fresh and frozen food products that are transported on the top side of the conveyor.

17. The system of claim 15, further comprising a sensor configured to provide information relating to the translational speed of the conveyor;
wherein the controller is coupled to the sensor and receives the information relating to the translational speed of the conveyor, and is responsive to changes in the translational of the conveyor by altering a frequency of flashes directed to the bottom side of the conveyor.

18. The system of claim 15, wherein the controller receives information relating to a level of disinfection of the conveyor, and is responsive to changes in the level of disinfection of the conveyor by altering at least one member of a group consisting of a frequency of flashes directed to the bottom side of the conveyor and the energy level of the flashes.

* * * * *